United States Patent [19]

Woltosz

[11] 4,211,230
[45] Jul. 8, 1980

[54] ELECTROSURGICAL COAGULATION

[75] Inventor: Stanley N. Woltosz, Rochester, N.Y.

[73] Assignee: Sybron Corporation, Rochester, N.Y.

[21] Appl. No.: 929,730

[22] Filed: Jul. 31, 1978

[51] Int. Cl.² ............................................. A61N 3/04
[52] U.S. Cl. .............................. 128/303.17; 128/421;
331/78; 332/14
[58] Field of Search .................... 128/303.13, 303.14,
128/303.17, 421–423; 331/78; 332/14

[56] References Cited
U.S. PATENT DOCUMENTS

| 3,058,470 | 10/1962 | Seeliger et al. | 128/303.14 |
| 3,478,744 | 11/1969 | Leiter | 128/303.14 |
| 3,730,188 | 5/1973 | Ellman | 128/303.14 |
| 3,897,787 | 8/1975 | Ikuno et al. | 128/303.14 |
| 3,898,991 | 8/1975 | Ikuno et al. | 128/303.14 |
| 3,952,748 | 4/1976 | Kaliher et al. | 128/303.14 |
| 3,963,030 | 6/1976 | Newton | 128/303.17 |
| 4,000,489 | 12/1976 | Bench | 331/78 X |
| 4,030,501 | 6/1977 | Archibald | 128/303.14 |
| 4,034,762 | 7/1977 | Cosens et al. | 128/303.17 |
| 4,038,984 | 8/1977 | Sittner | 128/303.14 |
| 4,051,855 | 10/1977 | Schneiderman | 128/303.14 |

Primary Examiner—Lee S. Cohen
Attorney, Agent, or Firm—Theodore B. Roessel; J. Stephen Yeo

[57] ABSTRACT

In an electrosurgical device, a RF generator is pulse modulated during coagulating procedures. Pulse repetition rate is varied allowing the occasional interjection of relatively wide pulses of RF energy while still allowing sufficient cooling time to avoid cell volatilization. The result is efficient coagulation with minimal cutting.

10 Claims, 4 Drawing Figures

ELECTROSURGICAL COAGULATION

BACKGROUND OF THE INVENTION

This invention relates to electrosurgery and is more particularly concerned with electrosurgical coagulation.

The purpose of electrosurgery is to provide both coagulation and cutting of living tissue during surgical procedures. Coagulation is the stoppage of blood and other fluids flowing from or through the tissue and is accomplished in electrosurgery by the dehydration of cells. Cutting is the surgical incision or excision of tissue and is accomplished in electrosurgery by the volatilization of cells. Hemostasis is a blend of both cut and coagulate.

These modes are very much functions of the peak and average power applied to the tissue. Let us consider an electrosurgical unit having an RF generator, the output of which is pulse modulated so as to provide an on-time of RF energy followed by an off-time. The RF energy is applied to the patient's tissue by means of electrodes. During the on-time the tissue is heated by the RF energy, while during the off-time the tissue cools.

For periodic modulation, duty cycle may be defined as the ratio of pulse on-time to the sum of pulse on and off time.

It is recognized that, for signals having a constant peak voltage, the energy transferred by the modulated RF signal is directly proportional to the duty cycle. Therefore, it has been necessary to provide higher voltage during coagulation than during cut so that high average power may be maintained for efficient coagulation while still allowing a cool off time sufficient to prevent cutting. Accordingly, the preferred conditions for electrosurgical coagulation has been an RF signal characterized by low duty cycle and high voltage.

An early electrical surgical device is the spark gap generator. This device has a peak voltage of up to 10,000 volts and a duty cycle of perhaps four percent. (The duty cycle of a spark gap can only be estimated, as the time between spark gap pulses may vary). The envelope of RF energy produced by the spark gap has been described as a damped sinusoid. The spark gap generator has enjoyed success for over 60 years, but due to maintenance, reliability, electrical interference, and other considerations it is becoming replaced by electronic electrosurgical units, and in particular, by solid state transistorized units. Transistorized units generally do not provide as high a voltage as does a spark gap generator and so the duty cycles of transistorized units are increased somewhat to provide a high power. This technique is limited as to how high the duty cycle can be increased because, even with lower voltage, too high a duty cycle will cause unwanted cutting.

It has been found that a duty cycle of 15% to 20% is usually suitable for coagulation. The relatively long offtime allows tissue to cool before volatilization can occur. A duty cycle of 60% or more is preferred for cutting. The high average power heats the tissue sufficiently to volatilize it. Duty cycles of about 50% to 60% are useful for hemostasis.

Prior Art

There are several ways that electronic RF generators have been modulated for coagulation purposes.

Seeliger et al in U.S. Pat. No. 3,058,470 describes an electrosurgical device which provides a damped high frequency current for coagulation.

Lieter, in U.S. Pat. No. 3,478,744 describes a high frequency current of 1 Mhz to 8 Mhz which is square wave modulated at a frquency between 1 to 200 kHz and delivered in low frequency bursts, as for example, an on-time of 0.1 seconds followed by an off-time of 0.4 seconds.

Ellman, U.S. Pat. No. 3,730,188, uses line frequency to sinusodially modulate an RF signal. Ellman recommends alternate half cycles for maximum coagulation.

Ikuno, et al., in U.S. Pat. Nos. 3,897,787 and 3,898,991, describe circuits which provide a high frequency signal which is amplitude modulated with a damped low frequency signal.

Kaliher, in U.S. Pat. No. 3,952,748, describes a coagulating wave form as "essentally non-periodic". It appears that this refers to a wave form similar to that described by Lieter, wherein a modulated RF signal is delivered at lower frequency cycles of off and on times.

Newton in U.S. Pat. No. 3,963,030 uses a tuned circuit to produce an output of decaying amplitude.

Archibald in U.S. Pat. No. 4,030,501 describes a wave form similar to Lieter or Kaliher where a modulated RF signal is provided in low frequency groups of off-on periods.

Cosens, U.S. Pat. No. 4,034,762, Sittner, U.S. Pat. No. 4,038,984; Schneiderman, U.S. Pat. No. 4,051,855 are examples of electrosurgical circuits delivering pulse modulated RF signals wherein different duty cycles are selected for cut and for coagulation.

SUMMARY OF THE INVENTION

In brief, pulse modulated RF energy is used to coagulate tissue. The modulator is characterized as a series of random width pulses having random times between the starting of pulses. The preferred ratio of average width and average time between pulses is about 0.1. If 30 watts of RF energy is desired, the preferred parameters are 6 milliwatts power in an average pulse, an average pulse width of 20 milliseconds, and an average time between the start of pulses of about 200 milliseconds. For coagulation as well as other surgical procedures the power may be controlled by varying the number and width of pulses as well as pulse amplitude.

These functions may be realized by an electro-surgical apparatus or device having an RF oscillator, the output of which is modulated in accordance with a modulating signal with the desired characteristics of random pulse width and random time between start of pulses. The modulating signal may be generated by timing circuits connected to achieve the randomness.

IN THE DRAWINGS

DETAILED DESCRIPTION OF THE INVENTION

Recognizing the apparent paradox of providing wide pulses of RF energy for high power purposes while at the same time providing a low duty cycle for cooling purposes, there is provided a method, and a circuit for practicing the method, whereby a RF signal is pulse modulated with pulses of varying width and varying repetition rate so that an occasional pulse of relatively wide width is interjected, while still allowing sufficient cool off time to prevent cutting.

While the invention will be described in connection with a preferred embodiment and method, it will be understood that the description is not intended to limit the invention to that embodiment and method. On the contrary, it is intended to cover all alternatives, modifications and equivalents as may be included within the spirit and scope of the invention as defined by the appended claims.

Figure 1:
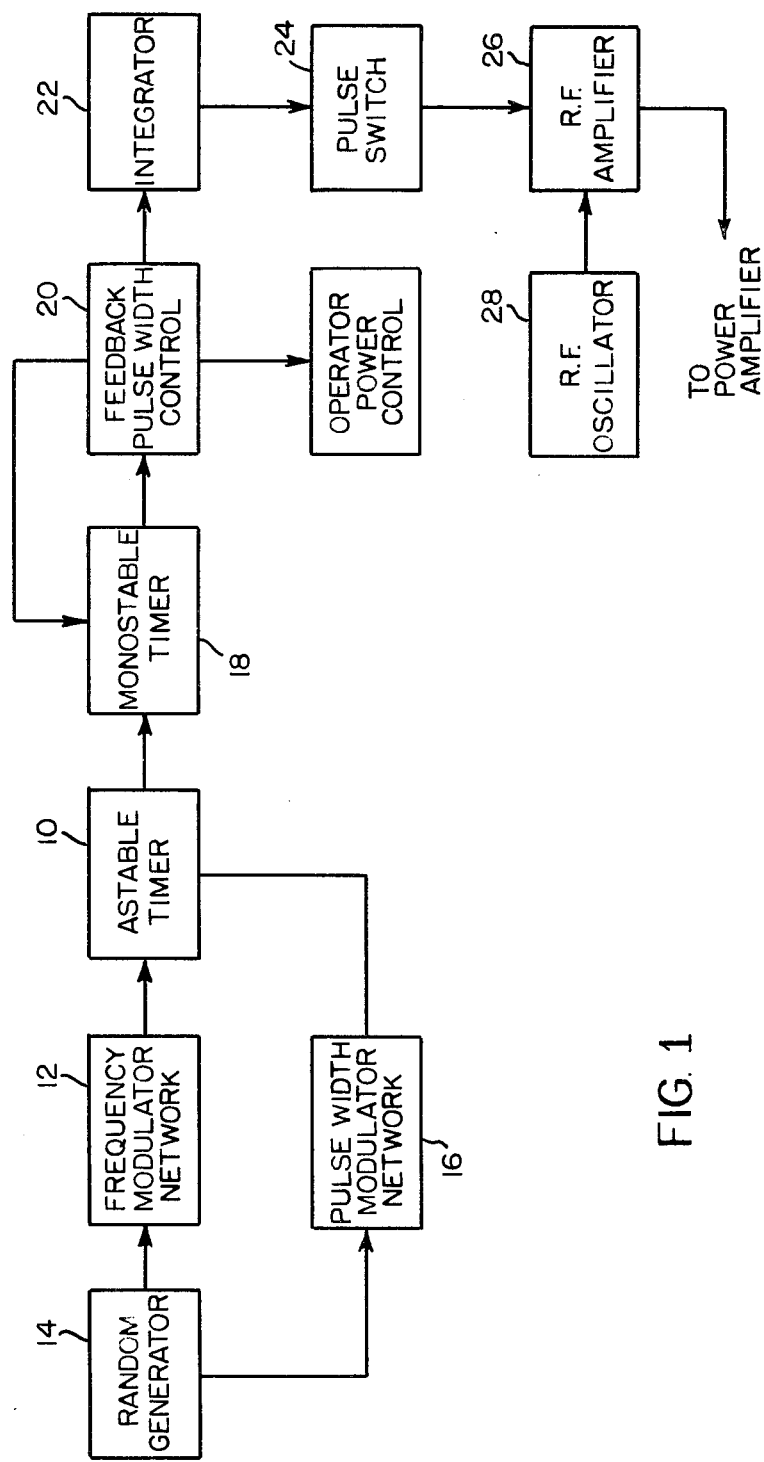
FIG. 1 is a block diagram of a circuit which embodies my invention.

FIG. 1 is block diagram of a circuit which is one embodiment of the invention. An astable timer 10 has an output of voltage pulses. The times between these pulses are determined by a frequency modulation network 12 which integrates voltage pulses from a random generator 14. When the integrated voltage reaches a first value, called the lower trip point, a pulse will start at the output of the astable timer. When the integrated voltage reaches a second value, called the upper trip point, the pulse will stop. In this way, the frequency modulation network varies both the starting time of a given pulse and the width of that pulse.

The upper trip point, at which point the pulse is turned off, may be a constant or varied to provide additional variation of pulse width. This feature may be realized by adding to the astable timer 10, a pulse width modulation network 16 which varies the upper trip point in relation to the random generator 14.

The output pulse of the astable timer 10 is used to trigger a monostable timer 18 thereby instigating an output pulse from the monostable timer 18. The length of this pulse is affected by width control circuitry 20 which has the effect of increasing or decreasing the pulse width. The pulses from the monostable timer 18, as modified by control circuitry 20, are integrated by integrator 22. The integral is used to turn on a switch 24 which modulates an RF amplifier 26 driven by oscillator 28. The envelope of the modulated RF wave will be a series of pulses having varied on and off times and varied rate of repetition.

Figure 2:
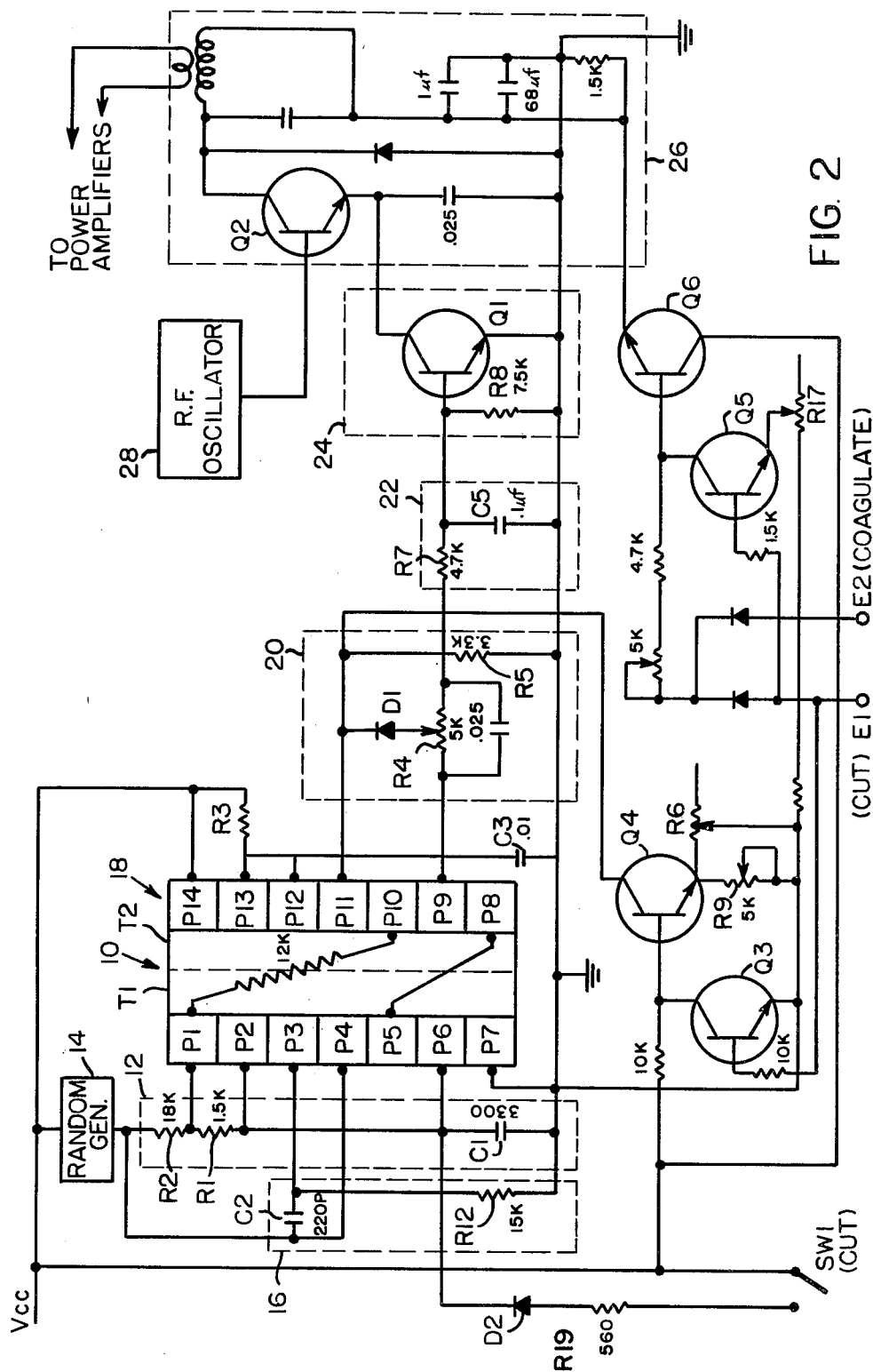
FIG. 2 is a schematic representation of the circuitry outlined in FIG. 1.

Reference is now made to FIG. 2, which is a schematic showing in detail the components of block diagram in FIG. 1.

The preferred circuit uses two 555 timer circuits. A model 556 timer, which is a dual 555 in a single package may be used. Pin descriptions used in this specification correspond to a 556 timer.

To understand this circuit, the properties of a 555 timer should be appreciated. The 555 timing circuit is a stable controller capable of producing accurate time delays or oscillations. Timing is provided by an external resistor and capacitor for each timing function. The circuits may be triggered and reset on falling waveforms.

In addition to Vcc and ground, each timer has the following pins: discharge; threshhold; control voltage; reset; output; and trigger. While the internal workings of each 555 timer is not necessary for the understanding of this invention, the functions of these pins should be understood. Discharge pin is normally in communication with ground. A positive voltage at the reset pin enables the timer to function in response to voltages at other pins. The appearance of a negative going pulse at the trigger pin disconnects discharge pin from ground. This normally allows an external capacitor to charge, gradually increasing the voltage appearing at threshold pin. During this time, there is no output voltage at the output pin. Only when the voltage at the threshold pin reaches a lower trip point output voltage appears at the output pin. The output voltage, when it appears, is approximately equal to Vcc. The control pin voltage defines the upper trip point. When the voltage at the threshold pin reaches the upper trip point the output drops to zero and the discharge pin is again connected to ground.

Resistance internal to the 555 circuit will normally make the upper trip point $\frac{2}{3}$ Vcc and the lower trip point $\frac{1}{3}$ Vcc. This voltage relationship to Vcc may be modified by applying a voltage directly to the control pin as the upper trip point is always equal to the voltage at the control pin. The lower trip point voltage is always $\frac{1}{2}$ voltage of the upper trip point voltage.

The above functions are true for both 555 timers T1, and T2 of the circuit.

The preferred circuit also uses a random noise generator 14 for producing a series of equal amplitude pulses of varying width. A suitable noise generator is a MM5837 digital noise source which uses a 15 bit shift register as part of suitable random sequence generator having a repeat cycle between 1.1 second and 2.4 seconds. The cycle effect is an artifact of the scheme used to generate the white noise. The generator is therefore actually a pseudorandom sequence generator. The noise appears to be random within a small period of time but does repeat with the cycle of the random generator. The recurrence of the noise series does not appear to effect the circuit, so it should be realized that a true random noise generator could be used in place of this device, and henceforth no distinction will be made in the specification or the claims between pseudorandom and truely random noise.

Figure 3:
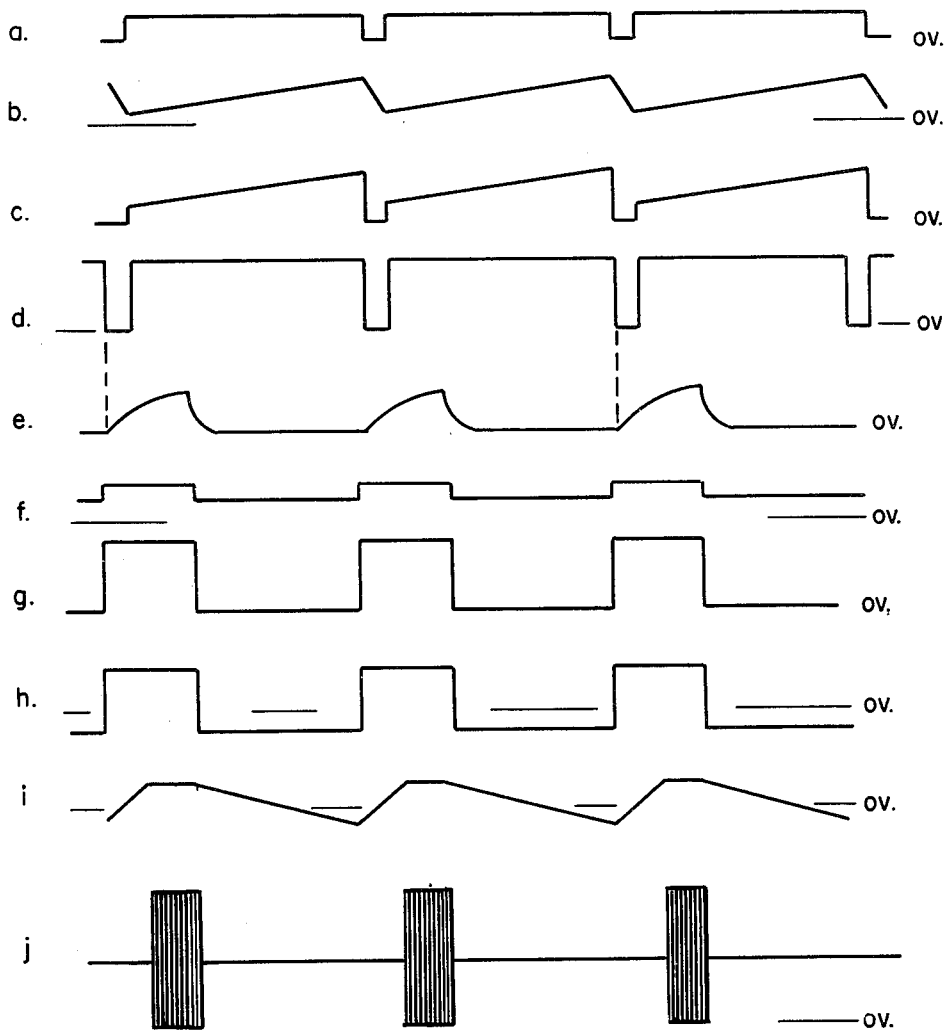
FIG. 3 represents waveforms of voltages appearing at selected points in the circuitry of FIG. 2.
Figure 4:
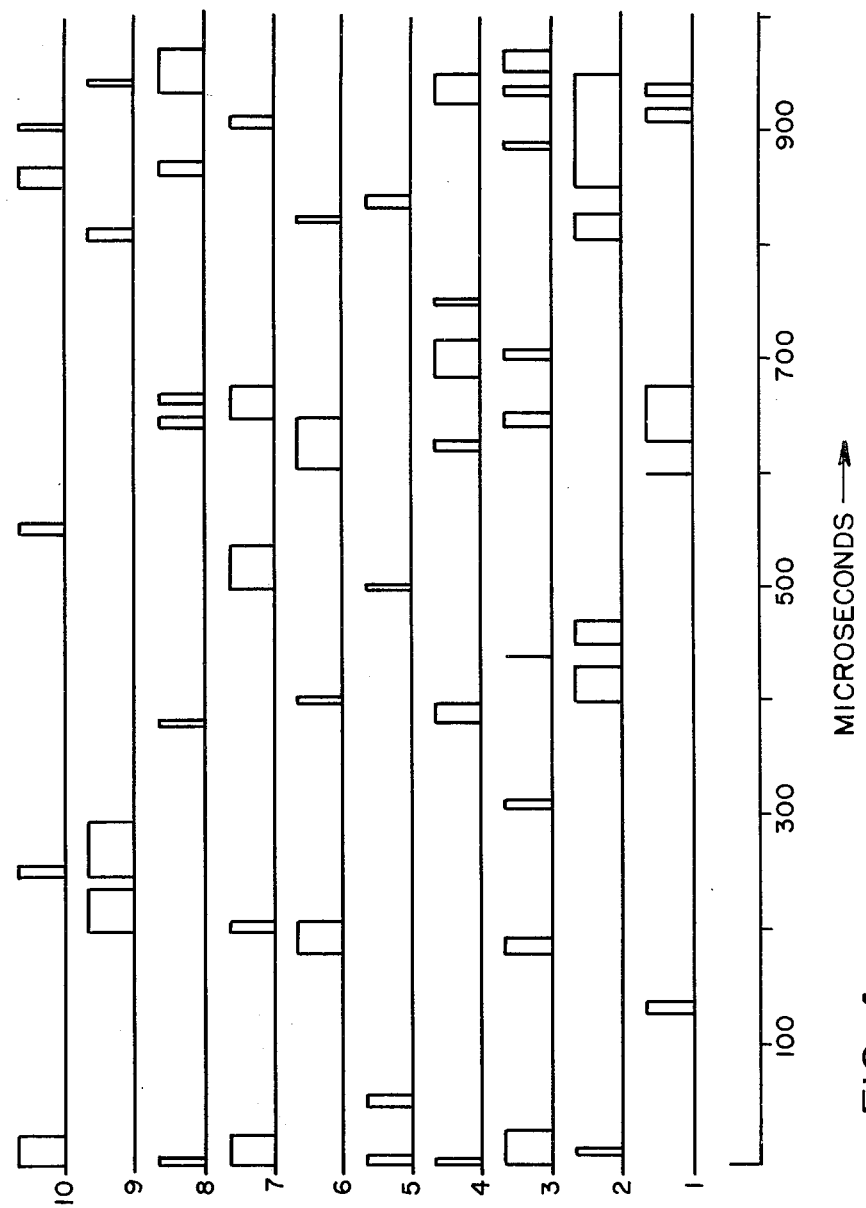
FIG. 4 illustrates the envelope of RF energy sampled at the output of the electrosurgical unit.

The circuit will first be described for coagulation procedures. FIG. 3 represents selected waves appearing in the circuit. As an aid to understanding the circuit, the output of noise generator 14 is shown (3a) having pulses of equal width. Actually the pulses will have random widths and the coagulating RF waveshape will also have random pulse widths as seen in FIG. 4.

The circuit of FIG. 2 is normally set for coagulation. A positive voltage applied to E2 switches on transistor Q6. Components C1, R1 and R2 form the frequency modulator circuit 12 of FIG. 1 and are in series to the output of noise generator 14 so that a pulse from 14 will charge capacitor C1 through resistors R1 and R2. Capacitor C1 is connected to threshold pin P2 and trigger pin P6 of timer T1 so any charge on C1 will appear at both pins, P2 and P6.

The reset pin P4 is connected to the output of generator 14. In order for timer T1 to function, a voltage from 14 must be present at P4. Pulses from generator 14 will appear at reset pin 4 and at trigger pin 6 to enable timer T1, as well as to charge C1 through resistors R1 and R2.

When the charge (3b) across C1, as measured at threshold pin P6, equals the low trip voltage of timer T1, an output voltage (3d) will appear at the output pin P5. This output voltage will remain until the occurrence of either of two conditions; the removal of the voltage at reset pin 4, or when the charge across C1 reaches the upper trip point voltage.

Thus, the output of timer T1 is comprised of pulses that terminate with the termination of the corresponding pulse from generator 14 or when the charge of C1 equals the voltage at control pin P3, whichever occurs first. This arrangement produces frequency modulation related to the pulse widths of generator 14.

As an additional feature of the invention, a capacitor C2 and a resistor R12 may be connected in series between generator 14 and ground. The junction of C2 and R12 is connected to the control pin P3. The voltage at control pin P3 is determined by capacitor C2 and resistor R12 which form the pulse width modulation network 16 of FIG. 1. The upper trip voltage is equal to the voltage across R12 and will be a variable enhancing pulse width modulation.

When the output voltage (3d) at output P5 falls, circuitry internal to timer T1 grounds the discharge pin P1 causing the voltage (3c) at P1 to drop abruptly. Capacitor C1 will then tend to gradually discharge (3b) through resistor R1 and P5 until the timer T1 is again reset and triggered by pulses from generator 14.

The discharge pin, P1, of timer T1, is connected to reset pin P10 of the second timer T2 so that timer T2 is operational only when discharge pin P1 is ungrounded (3c).

It has been shown that timer T1 is arranged in an astable configuration and will have an output at pin P5 comprised of pulses that are both frequency and width modulated.

The output, P5, of timer T1 is connected to the trigger P8 of second timer 18. The negative going termination of an output pulse (3d) from timer T1 triggers timer T2. Capacitor C3 is connected to the threshold pin P12 and the discharge pin P13, and is charged from Vcc through resistor R3. The voltage (3e) across C3 will rise, and upon reaching the lower trip point of timer T2, an output voltage will appear at the output of timer T2. This output voltage (3g) will remain until the voltage at the threshold pin P10 reaches the upper trip point, at which time capacitor C3 will discharge (3e) through discharge pin P13. This arrangement provides monostable operation, which means that timer T2 will have an output voltage (3g) at output pin 9 for the time between trip points or until discharge pin P1 is again grounded.

The lower and upper trip points of timer T2 are determined by the positive voltage at control pin P11 (3f). An increase in the voltage will raise both trip points, delaying the start of the monostable operation but increasing the pulse width. Conversely, a decrease in voltage will lower the trip points, advancing the start of the monostable operation but decreasing pulse width.

A feedback voltage from output pin P9 to control pin P11 is obtained from feedback circuit have resistor R4 and diode D1. The voltage at control pin P11 is also determined by the values of resistors R5 and R9 and variable resistor R6, assuming transistor Q4 is conducting. Resistor R6 is an operator control used to increase power setting, by increasing pulse width, to an output power that satisfies some surgical requirement. The unit is calibrated by setting R6 to its minimum position and adjusting R4 for a zero width pulse. Resistor R6 is then set to its maximum value and resistor R9 is adjusted to obtain a voltage (3h) resulting in the maximum desired coagulating pulse width, limiting thereby the maximum power. As will be discussed next in more detail, the setting of control resistor R6 will vary the number and widths of pulses at the output of the electrosurgical device, thereby controlling the coagulating power.

The output of the second timer T2 is modified by the feedback circuit, and is AC and DC coupled to a low pass R-C integrator having resistor R7 and capacitor C5. The integrator tends to shape the noise spectrum somewhat. Capacitor C5 is connected to the base of switching transistor Q1 and to parallel resistor R8. When the total AC and DC voltage across C5 (3i) reaches about 2 volts transistor Q1 will conduct, clamping the voltage across C5 to about 2 volts. The DC component of voltage of C5 is partially determined by the setting of R6, which also provides feedback voltage to control pin P11 of timer T2. The DC level will determine how fast the AC component reaches the 2 volts necessary to cause Q1 to conduct.

If control R6 were adjusted for more power the DC would be higher level therefore more pulse peaks would cause Q1 conduction while original pulses occurring before the added DC would be wider. The expansion of "on time" plus the additional peaks causing conduction of Q1, are amplified and provides more power at collector of Q2. Therefore, the additional random pulse widths and the additional pulses obtained by this adjustment causes the available power output to increase as a result of an increase of REP rate.

Conversely, reduction of power output by adjustment of R6, lowers the DC and AC provided to Q1 base.

The narrow pulses will be below the threshold level and will not cause Q1 conduction. The wider pulses would now become narrower, due to faster rise and fall times, and result in lower average RF power output. It is possible to reduce the DC and AC level where no conduction of Q1 is possible, resulting in zero RF power.

Internal adjustment R9 will adjust the average of all the variables and place them in the range of operator control R6. This adjustment limits the maximum amount of average pulses presented to base Q1 therefore clamping the maximum power obtainable.

Meanwhile, C5 will tend to discharge through resistor R8. When the voltage falls below 2 volts, Q1 will turn off until C5 is sufficiently recharged.

In FIG. 3 it is seen that the envelope of RF energy (3j) corresponds to the on and off state of Q1. Therefore, transistor Q1 functions as a modulator and the voltage (3i) across capacitor C5 as a modulating signal. As the setting of R6 affects turn on and turn off times, will affect the number and width of modulated RF pulses.

At the termination of a pulse, capacitor C5 will discharge through parallel resistor R8, and Q1 will switch off until C5 is again recharged to about 2 volts.

In FIG. 3 it is seen that the envelope of the modulated RF signal (3i) corresponds to the on and off states of transistor Q1, which may be described as a switch or a modulator of the RF energy.

Relating to FIG. 2, an oscillator 28 generates a signal at a radio frequency (RF) such as 1.75 Mhz. The RF signal is amplified by amplifier 26, the output of which is coupled by a transformer to power amplifiers and applied to the patient.

Amplifier 26 is operational only when switch Q1 is on, providing a DC ground to the emitter of transistor Q2 of RF amplifier 26. This action modulates the output RF signal in response to the modulator signal applied to Q1.

In FIG. 4 it is shown that the amplified RF signal during coagulation consists of random on-time random repetition rate and random off-times. A relatively long pulse width, which represents a large amount of energy, may be followed by a long off-time, allowing the tissue to cool, thereby providing both sufficient power to dehydrate and catalyze or coagulate tissue while allowing sufficient cooling time to prevent volatilization and resulting cutting.

To allow full power to reach the RF amplifier, a positive voltage is switched to E2 presenting a positive voltage to the base of transistor Q6, putting Q6 in conduction. Normally conducting Q4 connects R9 and operator control R6 at pin 11 of the 556 timers allowing feedback voltage control. As previously stated, R6 is set for zero power output R4 is internally adjusted for exactly zero output. R6 is set to maximum power output, requiring internal adjustment of R9 to limit maximum power.

Operator control R6 will now present to Q1 a random quantity and random width pulses, proportionate to knob rotation. Minimum power will produce minimum pulses, whereas rotation toward maximum power increases number of pulses and their widths.

The circuit has been described with the circuit arranged in a coagulation mode. Additional controls will now be described which allow the circuit to function in a cut mode or a hemostasis mode as well as the coagulation mode. For the hemostasis waveshape, the voltage on E2 is removed and placed on E1, allowing transistor Q3 to conduct and stopping Q4 from conducting, making R9 and R6 inoperative.

Q5 is also made to conduct, allowing R17 to control the voltage on the base of Q6. Increasing the base voltage causes Q6 to conduct more, allowing more DC voltage on the collector of Q2 increasing its amplification thereby placing more oscillator voltage into T1. When Q4 is made to stop conducting, the voltage division by R9 and R6 is negated and the average time constant of R3, C3 prevails. This condition allows wide pulse widths to 50 to 60% duty cycle and some volatilization (cutting) as well as coagulation will occur.

The "Hemostasis" waveshape has the general randomness of the coagulation waveshape, but with the extended pulse width, becomes a blend of cutting and coagulation waveshapes. Power control is by operator control of R17, allowing amplitude variations of power output.

To use the pure cut waveform an operator controlled switch, SW1, is placed in the cut position. This places a positive DC voltage on pin 6 via R19 and D2 stopping the operation of the random pulse generator.

Under these conditions, output pin 9 has a constant positive voltage output and applied to the base of Q1, causing it to conduct, which in turn causes Q2 to amplify the oscillator signal on its base. Power control is by amplitude changes using R17 variation.

The RF waveform is pulse modulated so as to provide random pulse width, random off time, and random repetition rate having occasional high energy densities while still allowing cooling time, results in a distinct improvement of coagulation.

The method of this invention is an improvement over previous methods which used set pulse width and constant repetition rate.

For the purpose of comparing methods, 30 watts is chosen to be the average RF power delivered to the tissue. In the old method, using constant pulse width and time between start of pulses, these values are typical:

Constant pulse width=11.1 microseconds
Time between start of pulses=55.5 microseconds
Duty cycle=0.2
Peak Power=average power/duty cycle=150 watts peak power
Watts/Pulse−30 watts×55.5×10−6−1.7 milliwatts The OFF to ON ratio is 4 to 1. The cooling time being 4 times the energy producing period.

Referring again to FIG. 4, the coagulation waveshape is seen to be random in pulse width, and random in time between pulses. In a sample of ten, an average time between pulses and average pulse widths were taken for each 1 millisecond scan. The total of ten scans were averaged in these characteristics and the mean of the averages are used to calculate peak power.

Ave pulse width=19.6 microsecond are approximately 20 microseconds

Ave time between start of pulses=195 microseconds are approximately 200 microseconds Duty Cycle=20/200=0.1
Peak Power=Ave Power/Duty Cycle=30 watts/0.1=300 watts
Watts/Pulse=30×200 10−6=6 milliwatts For the same average power, the peak power has doubled mainly by having the average pulse width increased. Clinically it has been found that the OFF times are so large that cells will not volatize. The average OFF time to average ON time is now 9 to 1. There are 9 times the cooling periods for each energy period.

Interjecting a low proportion of pulse widths greater than 20% (to boost power) will still allow sufficient OFF periods to prevent volatization.

Conclusions reached clinically and mathematically found instantaneously exceeding maximum pulse widths (beyond approximately 15 to 20%) are not detrimental and will not cause volatization if the OFF times are sufficient to cool cells. Wider pulse widths therefore may be proportionately inserted in the coagulation waveshape.

This invention has a distinct advantage of power control in that during coagulation, the operator may change quantity and proportionately vary widths of pulses that correspond to power. This is an advantage for pinpoint coagulation using needle electrodes, since normal high voltage is maintained, the power is decreased by using fewer cycles resulting in small scale coagulation with less burn. Conversely, an increase in power is good for spray area coagulation due to longer cooling periods. Amplitude control may also be used or combinations of amplitude and switching rate to obtain power control.

For a hemostasis waveshape, the coagulation waveshape has its random duty cycle remain the same, but its pulse width is extended by 50 to 60% to permit volatization. This waveshape is a blend of coagulation and cutting waveshapes, has as its terminology "Hemostasis" and as generated is used for a cutting-coagulating current for some surgical procedures.

Hemostasis waveshapes have the ability to cut and sear or coagulate simultaneously. This waveshape in general surgery may be used in heavy bleeding areas where cutting with hemostasis will tend to coagulate small bleeders during the cutting process. A hemostasis waveform will have the general periods of the coagulating waveform with the maximum pulse widths increased to 50 or 60%. Power control is preferable, but not limited to amplitude variations during hemostasis and cut surgery.

Thus it is apparent that there has been provided, in accordance with the invention, a method and circuit for this practice of electrosurgical coagulation that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A method for the electrosurgical coagulation of tissue comprising the steps of:
   (a) modulating RF energy into a series of pulses having random pulse widths and random time between the start of individual pulses; and
   (b) applying the modulated RF energy to tissue so that said tissue is coagulated in response to the modulated RF energy.

2. The method of claim 1 wherein the ratio of average pulse width to the average time between the start of pulses is approximately 0.1.

3. The method of claim 2, wherein the average RF energy used for coagulation is approximately 30 watts; and
   (a) the average power per pulse is approximately 6 milliwatts;
   (b) the average width per pulse is approximately 20 milliseconds; and
   (c) the average time between the start of pulses is approximately 200 milliseconds.

4. A method of adjusting the RF energy applied to tissue during surgical procedures, comprised of the steps of:
   (a) providing RF energy in a series of pulses, said pulses having random pulse widths and said series having an average quantity of pulses per unit of time;
   (b) applying said RF energy to tissue undergoing surgical procedures;
   (c) increasing both the average pulse width and quantity of pulses for an increase in RF energy; and
   (d) decreasing both the average pulse width and quantity of pulses for a decrease in RF energy.

5. The method of claim 4 wherein the pulses are maintained to be of substantially equal amplitude.

6. The method of claim 4 wherein the amplitude of the pulses is varied.

7. A method for the electrosurgical hemostasis of tissue comprising the steps of:
   (a) modulating RF energy into a series of pulses having random pulse widths and random times between the start of the pulses; and
   (b) applying the modulated RF energy to tissue so that said tissue undergoes hemostasis in response to the modulated RF energy.

8. Apparatus for electrosurgical procedures comprised of:
   means for providing a modulated RF signal characterized by having random pulse widths and random times between the start of individual pulses;
   means for amplifying said modulated RF signal characterized by having random pulse widths and random times between the start of individual pulses;
   means for amplifying said amplified modulated RF signal to a electrosurgically acceptable peak power level;
   means for the peak power level amplified modulated RF signal to be in electrical communication with electrosurgical electrodes; and
   means for controlling the ratio of the average pulse width to the average time between the start of pulses thereby controlling the average power of the peak power level amplified modulated RF signal.

9. Electrosurgical apparatus for coagulating tissue comprising:
   a random noise generator for providing an output of a series of pulses having random widths;
   a frequency modulator having an input in communication with the output of the random noise generator and having an output representing the integral sum of one or more of the pulses provided by the random noise generator;
   an astable timer in communication with the output of the frequency modulator and providing an output voltage when the output voltage of the frequency modulator is between a lower trip voltage and a higher trip voltage;
   a monostable timer in communication with the output of the astable timer, for providing an output voltage for a time period upon being triggered by the output of the astable timer;
   means for varying the length of the time period of the output of the monostable timer;
   an integrator in electrical communication with the output of the monostable timer, for producing a modulating signal representing an integral of the output of the monostable timer;
   a modulator in communication with the intergration, and responsive to, the modulating signal;
   an RF generator for generating an RF signal, the RF generator and modulator being connected so that the RF signal is modulated in response to the modulating signal; and
   means for putting the RF signal in electrical communication with at least one electrode in proximity to tissue undergoing coagulation.

10. The electrosurgical apparatus of claim 9 which further comprises means to vary the lower and higher trip voltages of the astable timer.

* * * * *